US011432892B1

(12) United States Patent
Turgeman et al.

(10) Patent No.: US 11,432,892 B1
(45) Date of Patent: Sep. 6, 2022

(54) SYSTEMS AND METHODS FOR CUTTING AN ANATOMICAL ELEMENT

(71) Applicant: Mazor Robotics Ltd., Caesarea (IL)

(72) Inventors: Avi Turgeman, Beer Yaakov (IL); Omer Ravid, Pardes-Hana (IL)

(73) Assignee: Mazor Robotics Ltd., Caesarea (IL)

(*) Notice: Subject to any disclaimer, the term of this patent is extended or adjusted under 35 U.S.C. 154(b) by 0 days.

(21) Appl. No.: 17/190,289

(22) Filed: Mar. 2, 2021

(51) Int. Cl.
*A61B 17/16* (2006.01)
*A61B 34/30* (2016.01)
*A61B 17/00* (2006.01)

(52) U.S. Cl.
CPC .......... *A61B 34/30* (2016.02); *A61B 17/1626* (2013.01); *A61B 17/1633* (2013.01); *A61B 17/1671* (2013.01); *A61B 2017/00991* (2013.01); *A61B 2217/005* (2013.01); *A61B 2560/0475* (2013.01)

(58) Field of Classification Search
CPC ................................................... A61B 34/30
See application file for complete search history.

(56) References Cited

U.S. PATENT DOCUMENTS

| 5,609,603 | A | 3/1997 | Linden |
| 2019/0083191 | A1 | 3/2019 | Gilhooley et al. |
| 2020/0229878 | A1* | 7/2020 | Finley .................... A61B 34/20 |
| 2020/0261176 | A1* | 8/2020 | Kapadia ................ A61B 34/30 |
| 2020/0268459 | A1* | 8/2020 | Noonan ................. A61B 34/30 |
| 2020/0281656 | A1* | 9/2020 | Torabi .................... A61B 34/25 |
| 2020/0297440 | A1* | 9/2020 | Forstein ............. A61G 13/0063 |
| 2020/0323540 | A1 | 10/2020 | Kang et al. |

FOREIGN PATENT DOCUMENTS

WO WO 2020/020898 1/2020

OTHER PUBLICATIONS

Extended Search Report for European Patent Application No. 22158826.2, dated Jul. 20, 2022, 12 pages.

* cited by examiner

*Primary Examiner* — Christian A Sevilla
(74) *Attorney, Agent, or Firm* — Sheridan Ross P.C.

(57) ABSTRACT

A system for cutting bone is provided and may comprise a cutting tool configured to rotate and a shield. The system may also comprise a first robotic arm configured to hold the cutting tool and a second robotic arm configured to hold the shield. A processor and a memory storing instructions for execution by the processor that, when executed, may cause the processor to cause the second robotic arm to orient the shield proximate an anatomical element along a cutting path of the cutting tool.

14 Claims, 7 Drawing Sheets

SYSTEMS AND METHODS FOR CUTTING AN ANATOMICAL ELEMENT

FIELD

The present technology generally relates to cutting an anatomical element, and relates more particularly to preventing collateral damage when cutting an anatomical element.

BACKGROUND

Surgical procedures may require removal of a portion of an anatomical element such as a bone. One or more tools may be used to remove the portion of the anatomical element. Surgical robots may assist a surgeon or other medical provider in using the one or more tools to carry out the surgical procedure, or may complete one or more surgical procedures autonomously.

SUMMARY

Example aspects of the present disclosure include:

A system for cutting bone according to at least one embodiment of the present disclosure comprises a cutting tool configured to rotate; a shield; a first robotic arm configured to hold the cutting tool; a second robotic arm configured to hold the shield; a processor; and a memory storing instructions for execution by the processor that, when executed, cause the processor to: cause the second robotic arm to orient the shield proximate an anatomical element along a cutting path of the cutting tool.

Any of the aspects herein, wherein the cutting tool is configured to extend in a first direction, wherein the shield comprises a first body configured to extend in a second direction and a second body coupled to the first body by a joint, the second direction distinct from the first direction, the second body configured to selectively rotate about the joint.

Any of the aspects herein, wherein the cutting tool comprises a first tube nested inside of a second tube, the first tube having a distal end comprising a set of cutting teeth.

Any of the aspects herein, further comprising: a vacuum source configured to apply a suction force to the cutting tool to suction anatomical particles through the first tube. Any of the aspects herein, wherein the first tube is configured to extend axially.

Any of the aspects herein, wherein the shield has a width at least as wide as a diameter of the cutting tool.

Any of the aspects herein, wherein a diameter of the cutting tool is about 10 mm.

A system for cutting bone according to at least one embodiment of the present disclosure comprises a cutting tool supported by a robotic arm; a shield supported by the robotic arm; a processor; and a memory storing instructions for execution by the processor that, when executed, cause the processor to: cause the robotic arm to orient the shield proximate an anatomical element at a planned exit point of the cutting tool, and to control the cutting tool to cut through the anatomical element toward the planned exit point.

Any of the aspects herein, wherein at least one of a cutting tool and the shield is configured to extend telescopically.

Any of the aspects herein, wherein the cutting tool comprises a first tube nested inside of a second tube, the first tube configured to extend from the second tube, the first tube having a distal end comprising a set of cutting teeth.

Any of the aspects herein, wherein causing the robotic arm to orient the cutting tool includes extending the second tube to orient the cutting tool at the side of the anatomical element, wherein the first tube does not extend past the second tube.

Any of the aspects herein, wherein the shield comprises a first segment and a second segment disposed at an angle to the first segment.

Any of the aspects herein, wherein the second segment is perpendicular to the first segment.

Any of the aspects herein, wherein the first segment and the second segment are fixed.

A system for cutting bone according to at least one embodiment of the present disclosure comprises a cutting tool; and a shield positionable independently of the cutting tool and comprising: a first segment; and a second segment coupled to the first segment by a joint, the second segment having a selectively adjustable angle relative to the first segment.

Any of the aspects herein, wherein the cutting tool comprises: a first tube having a distal end comprising a plurality of teeth; and a second tube, the first tube nested inside of the second tube, the first tube and the second tube configured to extend in an axial direction.

Any of the aspects herein, wherein the first tube is configured to move from a first orientation in which the cutting teeth are nested within the second tube to a second orientation in which the cutting teeth extend beyond the second tube.

Any of the aspects herein, wherein the cutting tool is configured to move in a first direction, wherein the shield further comprises a base, and wherein the first segment is selectively extendable from the base in a second direction distinct from the first direction.

Any of the aspects herein, wherein the cutting tool is configured to rotate, vibrate, or oscillate.

Any of the aspects herein, wherein the shield is configured to prevent further movement of the cutting tool in the first direction upon contact of the cutting tool with the shield.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
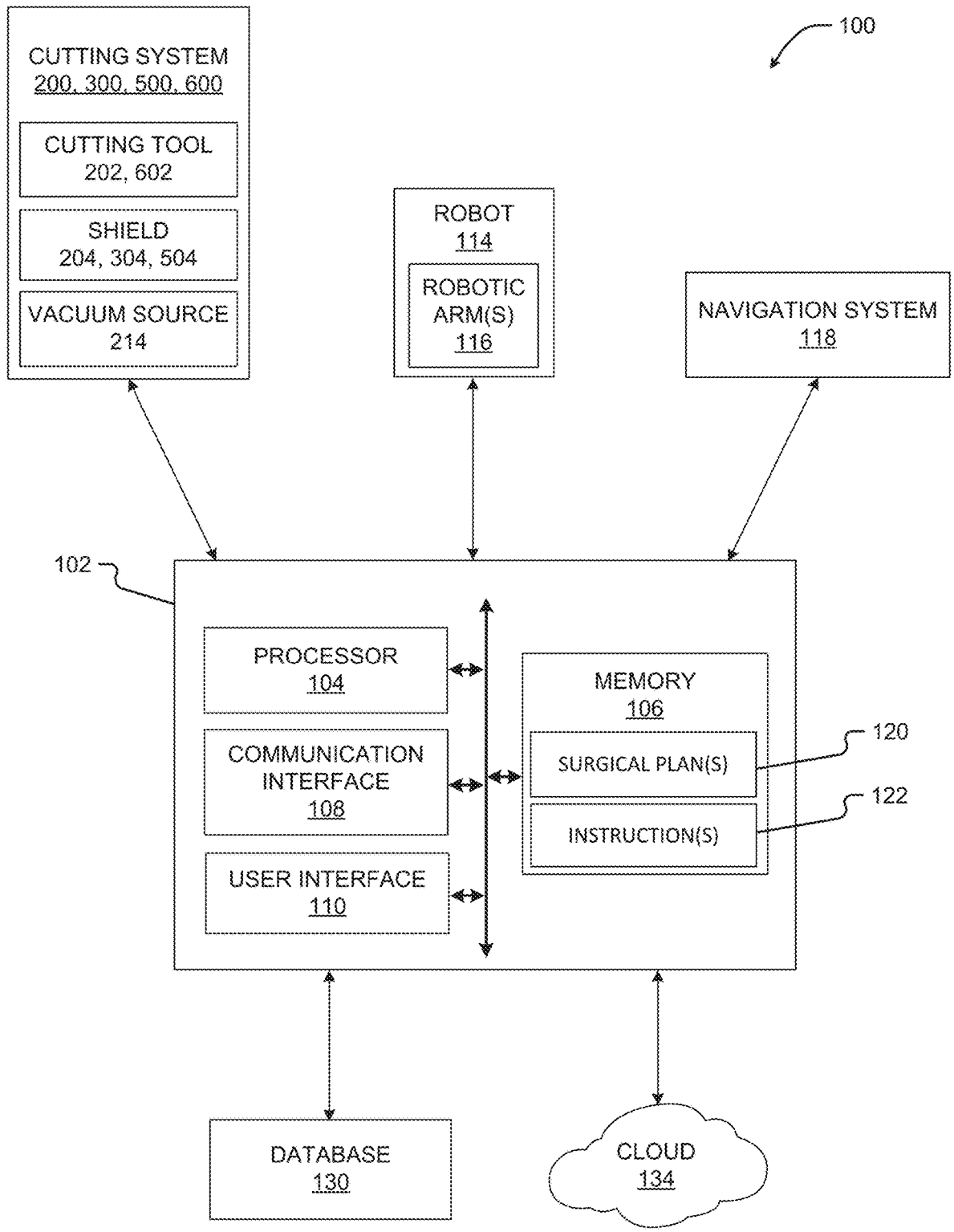
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Bone cutting or removal is a complex procedure with significant risk of harm to the spinal canal or other essential tissues of a patient, depending on the location of the bone being cut. Cutting or removal of a part of a vertebra is performed, for example, to relieve pressure on a nerve or ease a pain in the spine. It is desirable to avoid harm of surrounding dura matter or nerves during such cutting or removal of a portion of the vertebra. Thus, a safe cutting procedure using, for example, two robotic arms is provided.

In at least one embodiment, one robotic arm holds a cutting tool and another robotic arm holds a safety protection device or a shield. The robotic arms may move synchronously in a leader-follower (e.g., master-slave) manner. The leader robotic arm, which holds the cutting tool, may move along a planned trajectory for cutting the bone (e.g., the vertebra), while the follower robotic arm tracks the leader robotic arm with a maximum error of, for example, less than 1.5 mm. As such, the bone or a portion of the bone is removed under safe boundaries (and secured by the shield attached to the follower robotic arm). In such embodiments, an external navigation system or additional markers may not be used during the procedure.

The cutting tool may be a rotated, ring-shaped saw, located inside an external protection tube. While approaching an entry point at the anatomical element, the cutting edge may be covered in order to protect soft tissues. The cutting edge may then be exposed on the bone surface. The protection tool edge of the external protection tube may be a telescopic expandable tube, which may retract or extend according to the patient anatomy. The cutting tool may also be a drill bit or other cutting tool that is configured to remain in a retracted position during insertion toward a surgical site, and to then extend from the retracted position during use.

Embodiments of the present disclosure provide technical solutions to one or more of the problems of (1) cutting and/or removing bone or another anatomical element safely (e.g., without harming anatomical elements adjacent or otherwise proximate to the bone or other anatomical element), (2) safe bone or other anatomical element cutting using two robotic arms synchronously, (3) providing protection for a cutting mechanism during insertion of a cutting tool into patient anatomy, (4) preventing a cutting mechanism from causing damage to a patient's anatomy during insertion toward a surgical site; (5) inserting a shield or other protective barrier in a cutting path of a cutting mechanism to prevent the cutting mechanism from traveling too far along the path, and doing so in a minimally invasive surgical context; and/or (6) increasing patient safety during surgical operations.

Turning first to FIG. 1, a block diagram of a system 100 according to at least one embodiment of the present disclosure is shown. The system 100 may be used to cut or otherwise remove at least a portion of an anatomical element such as, for example, a vertebra, and/or carry out one or more other aspects of one or more of the methods disclosed herein. The system 100 comprises a bone cutting or partial anatomical element cutting system 200, 300, 500, 600 (described in detail with respect to FIGS. 2-6B below), a computing device 102, a robot 114, a navigation system 118, a database 130, and/or a cloud or other network 134. Systems according to other embodiments of the present disclosure may comprise more or fewer components than the system 100. For example, the system 100 may not include the robot 114, the navigation system 118, one or more components of the computing device 102, the database 130, and/or the cloud 134. Although referred to as a "bone" cutting system 200, 300, 500, 600 herein, embodiments of the present disclosure may also be used for cutting non-bone anatomical elements, including soft tissue anatomical elements.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the method 700 described herein, or of any other methods. The memory 106 may store, for example, one or more surgical plans 120 and/or one or more sets of instructions 122. Such instructions 122 may, in some embodiments, be organized into one or more applications, modules, packages, layers, or engines. The instructions 122 may cause the processor 104 to manipulate data stored in the memory 106 and/or received from or via the robot 114, the database 130, and/or the cloud 134.

The computing device 102 may also comprise a communication interface 108. The communication interface 108 may be used for receiving image data or other information from an external source (such as the robot 114, the navigation system 118, the database 130, the cloud 134, the bone cutting system 200, 300, 500, 600, and/or any other system or component not part of the system 100), and/or for transmitting instructions, images, or other information to an external system or device (e.g., another computing device 102, the robot 114, the navigation system 118, the database 130, the cloud 134, the bone cutting system 200, 300, 500, 600, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The robot 114 may be any surgical robot or surgical robotic system. The robot 114 may be or comprise, for example, the Mazor X™ Stealth Edition robotic guidance system. The robot 114 may be configured to position any component such as the cutting tool 202, 602, and/or the shield 204, 304, 504 at one or more precise position(s) and orientation(s), and/or to return the component(s) to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the bone cutting system 200, 300, 500, 600. In embodiments where the cutting tool 202, 602 and the shield 204, 304, 504 operate independently of each other, one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, a cutting tool 202, 602, a shield 204, 304, 504, a surgical tool, a surgical instrument, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm 116 (as well as any object or element held by or secured to the robotic arm 116).

In some embodiments, reference markers (i.e., navigation markers) may be placed on the robot 114 (including, e.g., on the robotic arm 116), the bone cutting system 200, 300, 500, 600, and/or any component thereof, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., the bone cutting system 200, 300, 500, 600) and the system can operate without the use of the robot 114 (e.g., with the surgeon manually manipulating the bone cutting system 200, 300, 500, 600 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the bone cutting system 200, 300, 500, 600, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, or other source) or for displaying an image and/or video stream from the one or more cameras or other sensors of the navigation system 118. In some instances, such as, for example, if it is not possible to determine an exact location of a tool tip with sensor data from the robot 114, then data from the navigation system 118 may be used to determine the location of the tool tip. The navigation system 118 may be configured to provide guidance to a surgeon or other user of the system 100 or a component thereof, to the robot 114, or to any other element of the system 100 regarding, for example, a pose of one or more anatomical elements, whether or not the cutting tool 202, 602, the shield 204, 304, 504, or any other tool is in the proper trajectory, and/or how to move the cutting tool 202, 602, the shield 204, 304, 504, or any other tool into the proper trajectory to carry out a surgical task according to a preoperative or other surgical plan such as the surgical plan 120. In some embodiments, the system 100 can operate without the use of the navigation system 118.

The system 100 or similar systems may be used, for example, to carry out one or more aspects of the method 700 described herein. The system 100 or similar systems may also be used for other purposes.

Figure 2:
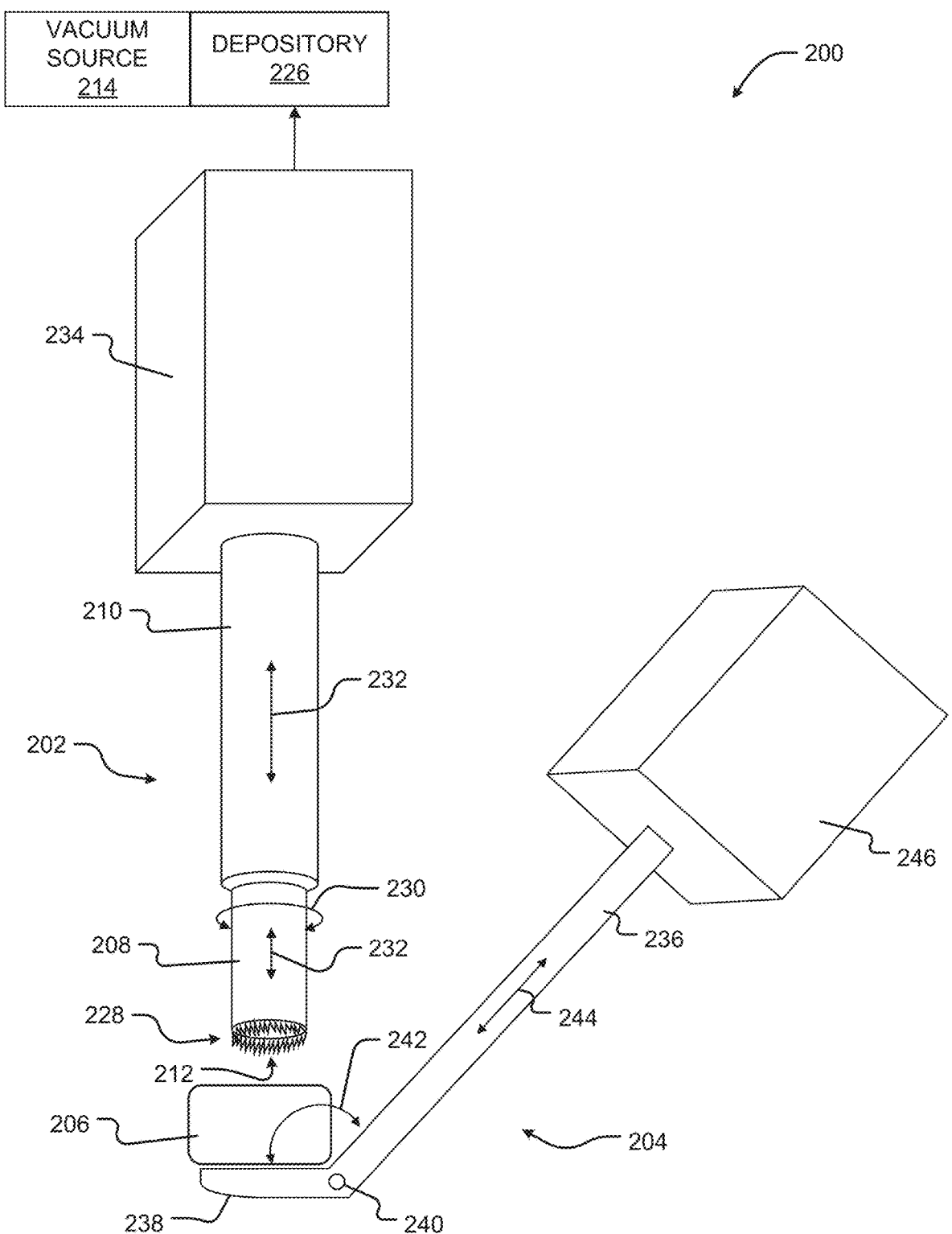
FIG. 2 is a schematic perspective view of a partial anatomical element cutting system according to at least one embodiment of the present disclosure.

Turning to FIG. 2, a schematic perspective view of a bone cutting system 200 is shown. The bone cutting system 200 may be used in a minimally invasive surgical procedure or an open surgery. For example, the system 200 may be used in a minimally invasive surgical procedure using two ports. Though the system 200 is referred to as a bone cutting system 200, it will be appreciated that the system 200 can be used to cut any anatomical element.

The system 200 includes a cutting tool 202 and a shield 204. During use, the shield 204 is positioned proximate an anatomical element 206 at a planned exit point of the cutting tool 202 such that when the cutting tool 202 exits the anatomical element 206 after cutting the anatomical element 206, the shield 204 protects the surrounding soft tissue (such as dura matter, a spinal cord, nerves, etc.) from the cutting tool 202. In other instances, the shield 204 may be positioned along any portion of a cutting path or trajectory of the cutting tool 202.

The shield 204 is separate from and therefore may be oriented independently of the cutting tool 202. As such, two incisions may be formed to each receive the cutting tool 202 or the shield 204, respectively, during a surgical procedure (such as, for example, a minimally invasive surgical procedure). In some embodiments, the cutting tool 202 may be oriented by a first robotic arm and the shield 204 may be oriented by a second robotic arm. The first robotic arm and the second robotic arm may be the same as or similar to the robotic arm 116 described above with reference to FIG. 1. In other embodiments, the cutting tool 202 and the shield 204 may be oriented by a user such as a surgeon or other medical provider. In further embodiments, one of the cutting tool 202 or the shield 204 may be oriented by a robotic arm such as the robotic arm 116 and the other one of the cutting tool 202 or the shield 204 may be oriented by a user.

The cutting tool 202 may have a width of about 10 mm in some embodiments. In other embodiments, the cutting tool 202 may have a width greater than or less than 10 mm. In the illustrated embodiment, the cutting tool 202 includes a first tube 208 nested inside of a second tube 210. The first tube 208 and/or the second tube 210 may be formed from any solid, biocompatible material such as metal, aluminum, stainless steel, steel, titanium, plastic (e.g., PEEK), or the like. In the illustrated embodiment, the first tube 208 includes a plurality of teeth 228 or serrations at a distal end of the first tube 208 for cutting the anatomical element 206. The plurality of teeth 228 may constitute serrations similar to a saw. In other embodiments, the first tube 208 may include any type and any number of cutters for cutting, scraping, drilling, or crushing the anatomical element 206. In some embodiments, the first tube 208 may be configured to rotate (for example, the first tube 208 may rotate as indicated by the arrow 230) to cut or scrape the anatomical element 206. In other embodiments, the first tube 208 may be configured to oscillate or vibrate (in any direction) to crush or otherwise cut into the anatomical element 206.

The first tube 208 and the second tube 210 are configured to extend telescopically in a first direction as indicated by the arrow 232. In some embodiments, the first tube 208 may extend a maximum distance of about 250 mm from the second tube 210. In other embodiments, the first tube 208 may extend a maximum distance greater than or less than 250 mm from the second tube 210. The first tube 208 and the second tube 210 may extend automatically (e.g., whether by an external or internal motor, a robotic arm such as the robotic arm 116 causing the first tube 208 and/or the second tube 210 to extend, and whether in response to a user input or otherwise) or may be extended manually by, for example, a user (such as a surgeon or other medical provider). During use, the first tube 208 may remain nested inside of the second tube 210 in a first position during insertion and positioning of the cutting tool 202 in a patient anatomy. In the first position, the plurality of teeth 228 do not extend beyond the second tube 210. In other words, the plurality of teeth 228 are not exposed. By nesting the first tube 208 inside of the second tube 210, the benefits are two-fold. The anatomical elements are protected from accidental damage by the plurality of teeth 228 and the plurality of teeth 228 are also protected from accidental damage by anatomical elements (such as bone). When the cutting tool 202 is in place (by way of positioning the cutting tool 202 and potentially extending the second tube 210 telescopically in the first direction), the first tube 208 may move to a second position in which the plurality of teeth 228 extend beyond the second tube 210. The first tube 208 may move to the second position by extending in the first direction.

The first tube 208 and/or the second tube 210 include a cannula 212 through which debris (such as anatomical particles resulting from cutting the anatomical element 206) may be removed. In the illustrated embodiment, a vacuum source 214 may provide a suction force to the cannula 212 to suction debris from the anatomical element 206 or the area surrounding the anatomical element 206 and through the cannula 212. The debris may be suctioned to a depository 226. The depository 226 may be directly attached to the cutting tool 202 or may be connected to the cutting tool 202 by a hose, tubing, or other connection through which debris may be delivered. In some embodiments, such as when the first tube 208 is replaced by a simple drill bit such as a drill bit 644 (as shown and described with respect to FIG. 6), the system 200 may not include the vacuum source 214 and/or the depository 226. In other embodiments, a fluid may be delivered to a cutting site to flush debris from the cutting site (whether with or without the depository 226 and/or the vacuum source 214).

As further shown in the illustrated embodiment, the first tube 208 and the second tube 210 extend from a cutting base 234. In some embodiments, the cutting base 234 may be supported by a robotic arm, such as the robotic arm 116, or by a user (such as a surgeon or other medical provider). In other embodiments, the cutting tool 202 may not include the cutting base 234 and the robotic arm or the user may support the cutting tool 202 at, for example, the second tube 210.

Still referring to FIG. 2, the shield 204 includes a first body or segment 236 coupled to a second body or segment 238 by a joint 240. The first segment 236 and/or the second segment 238 may be formed from any solid, biocompatible material such as metal, aluminum, stainless steel, steel, titanium, plastic (e.g., PEEK), or the like. The second segment 238 may have a selectively adjustable angle relative to the first segment 236. In other words, the second segment 238 may be selectively rotatable about the joint 240 as indicated by the arrow 242. The second segment 238 may rotate automatically (e.g., whether by an external or internal motor, and whether in response to a user input or otherwise) or may be rotated manually by, for example, a user (such as a surgeon or other medical provider).

The second segment 238 may be inserted into an incision while in a first position where the second segment 238 is substantially parallel to the first segment 236. In other words, the second segment 238 may have an angle substantially zero relative to the first segment 236. The first position provides for a narrow cross-section of the shield 204, thereby decreasing a needed diameter of an incision for insertion of the shield 204 and providing for simple insertion of the shield 204 into the incision. The second segment 238 may also be placed in the first position for storage of the shield 204. The second segment 238 may move or be moved to a second position after insertion of the shield 204 into a patient anatomy. The second position is defined by the second segment 238 being at an angle greater than zero relative to the first segment 236. The second segment 238 may also be locked in the second position so that the second segment 238 does not move. In some embodiments the second segment 238 does not move to the second position until the second segment 238 is oriented at or near the anatomical element 206. In other embodiments, the second segment 238 may move to the second position prior to being oriented near the anatomical element 206 and may move to the second position at any portion of a trajectory of the second segment 238.

In some embodiments, the first segment 236 may be configured to extend in a second direction different from the first direction, as indicated by the arrow 244. The first segment 236 may extend automatically (e.g., whether by an external or internal motor or a robotic arm such as the robotic arm 116 causing the first segment 236 to extend, and whether in response to a user input or otherwise) or may be extended manually by, for example, a user (such as a surgeon or other medical provider). In at least some embodiments where the first segment 236 is extendable, the first segment 236 may be selectively extendable from a shield base 246. In other embodiments, the first segment 236 may be fixed.

The second segment 238 may have a width at least as wide as a diameter of the cutting tool 202. In some embodiments, the width is about 10 mm. In other embodiments, the width is less than or greater than 10 mm. In some embodiments, the second segment 238 may also have a length of about 25 mm. In other embodiments, the length is greater than or less than 25 mm. The second segment 238 may also have a depth of about 4 mm. In other embodiments, the depth of the second segment 238 may be less than or greater than 4 mm.

The second segment 238 is dimensioned so as to block further movement of the cutting tool 202 when the first tube 208 contacts the second segment 238 (after having cut or drilled through the anatomical element 206). In other words, the shield 204 is sized so as to block and prevent further movement of the cutting tool 202 in the first direction (as indicated by the arrow 232) upon contact of the cutting tool 202 with the shield 204. Such blocking may prevent damage to surrounding soft tissue (e.g., dura matter, nerves, etc.) or other anatomical elements when cutting or drilling an anatomical element such as bone.

The dimensions of the second segment 238 may be selected, for example, based on the dimensions of the cutting tool 202, a flexibility and/or rigidity of the cutting tool 202, and/or a cutting speed of the cutting tool 202 (e.g., to ensure that the cutting tool 202 will not cut through the second segment 238 before being stopped). In some embodiments, the cutting tool 202 may be configured to only extend as far as the second segment 238, such that the cutting tool 202 is physically unable to cut through the shield 304.

In at least some embodiments where the cutting tool 202 and the shield 204 are oriented and controlled by a first robotic arm and a second robotic arm, respectively, the first robotic arm and the second robotic arm may move synchronously in a leader-follower manner. In such synchronous manner, the first robotic arm and the second robotic arm are controlled with a centralized computer such as, for example, the computing device 102. The computing device 102 may be exposed or in communication with all applicable sensor(s) and/or robot position(s), which enables the centralized computer to move the first robotic arm and the second robotic arm in a synchronous manner with a maximum tracking error, for example, of about 1 mm. The leader or the first robotic arm may move along a planned trajectory for cutting the anatomical element 206 while the follower or the second robotic arm may track the leader trajectory. In some embodiments, the follower or the second robotic arm may track the leader trajectory with a maximum error of about less than 1.5 mm. In other embodiments, the maximum trajectory may be about less than 2.5 mm, less than 2.0 mm, less than 1.0 mm, or less than 0.5 mm. In such embodiments, a navigation system such as the navigation system 118 may not be used.

Figure 3:
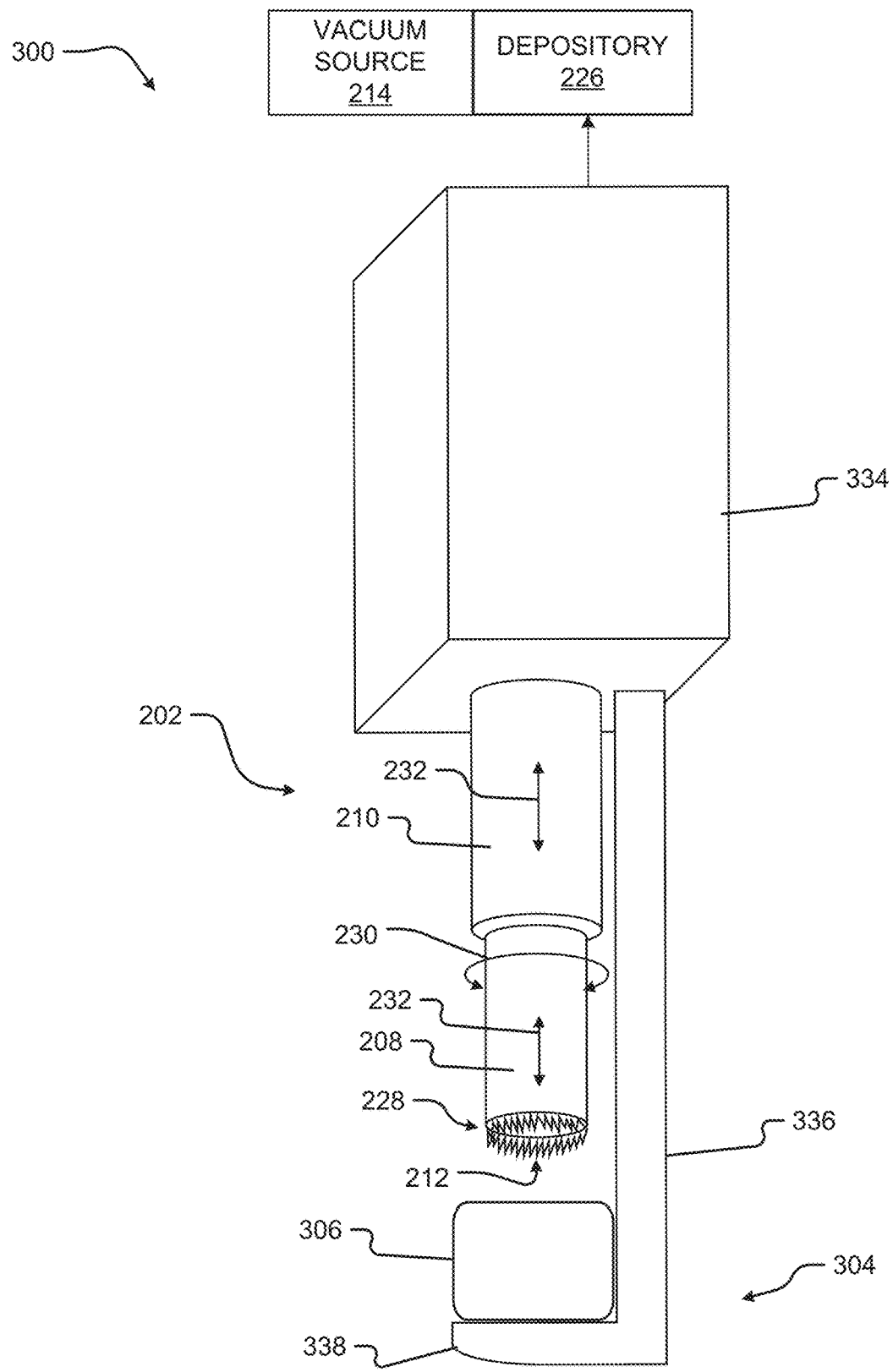
FIG. 3 is a schematic perspective view of a partial anatomical element cutting system according to at least one embodiment of the present disclosure.
Figure 4:
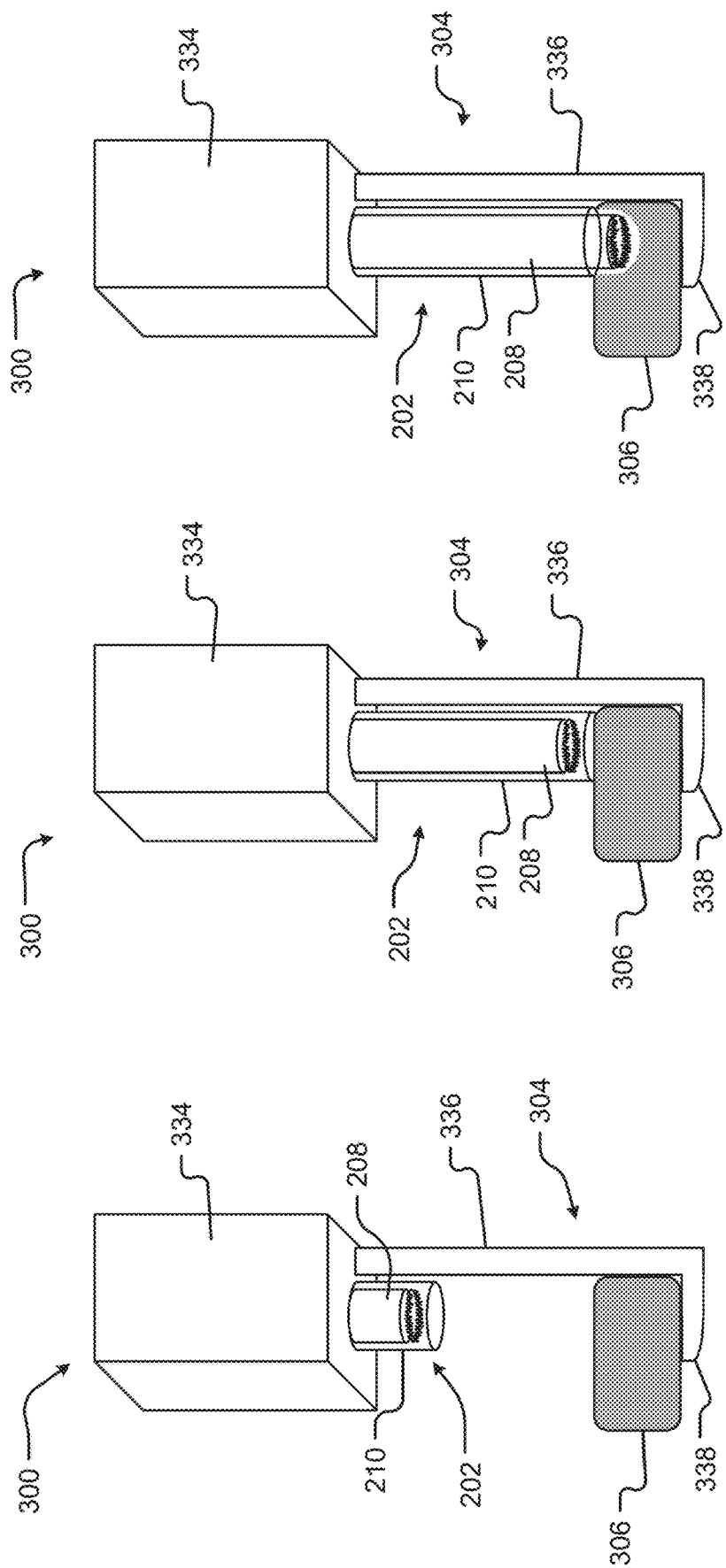
FIG. 4A is a schematic perspective view of the partial anatomical element cutting system of FIG. 3 in a first configuration.
FIG. 4B is a schematic perspective view of the partial anatomical element cutting system of FIG. 3 in a second configuration.
FIG. 4C is a schematic perspective view of the partial anatomical element cutting system of FIG. 3 in a third configuration.

Turning to FIG. 3, a schematic perspective view of a bone cutting system 300 is shown. The bone cutting system 300 may be used in a minimally invasive surgical procedure or an open surgery. Though the system 300 is referred to as a bone cutting system 300, it will be appreciated that the system 300 can be used to cut any anatomical element. Many components of the system 300 are the same as or similar to the components of the system 200, and are described above in connection with the system 200 such as, for example, the cutting tool 202, the vacuum source 214, and the depository 226. The bone cutting system 300 may be used in single-port minimally invasive surgeries.

The system 300 includes the cutting tool 202 and a shield 304. In some embodiments, the cutting tool 202 and the shield 304 may be oriented by a robotic arm that may be the same as or similar to the robotic arm 116 described above with reference to FIG. 1. In some embodiments, the system 300 may be supported and/or oriented by a single robotic arm and thus, may only require one patient incision during a surgical procedure (such as, for example, a minimally invasive procedure). Also in some embodiments, a pilot hole may be made to facilitate entrance of the cutting tool 202 and shield 304 into the patient's anatomy. In at least some embodiments, for example, the surgical procedure may include forming a pilot hole such that the tool 202 may enter the pilot hole with protection (by, for example, positioning the first tube 208 in the first position where the first tube 208 is nested inside of the second tube 210). In such embodiments, a port may be inserted into the pilot hole. The incision may be larger than the pair of incisions formed when using the system 200 as both the cutting tool 202 and the shield 304 are inserted into the same incision when using the system 300. In other embodiments, the cutting tool 202 and the shield 304 may be oriented by a user such as a surgeon or other medical provider.

The shield 304 includes a first body or segment 336 and a second body or segment 338. The first segment 336 and/or the second segment 338 may be formed from any solid biocompatible material such as metal, aluminum, stainless steel, steel, titanium, plastic (e.g., PEEK), or the like. In the illustrated embodiment, the first segment 336 extends from the base 334 at a fixed distance. In other embodiments, the first segment 336 may telescopically extend to and from the base 334, similarly to the first segment 236 described above with respect to FIG. 2.

In the illustrated embodiment, the second segment 338 is substantially perpendicular to the first segment 336. In other embodiments, the second segment 338 may be disposed at any angle relative to the first segment 336. Although the second segment 338 is fixed relative to the first segment 336 in the illustrated embodiment, in further embodiments, the second segment 338 may have a selectively adjustable angle relative to the first segment 336, similarly to the second segment 228 described above with respect to FIG. 2.

The second segment 338 may have a width at least as wide as a diameter of the cutting tool 202. In some embodiments, the width is about 10 mm. In other embodiments, the width is less than or greater than 10 mm. In some embodiments, the second segment 338 may also have a length at least as wide as the diameter of the cutting tool 202. In some embodiments, the length is about 25 mm. In other embodiments, the length is greater than or less than 25 mm. The second segment 338 may also have a depth of about 4 mm. In other embodiments, the depth of the second segment 338 may be less than or greater than 4 mm.

The second segment 338 is dimensioned so as to block further movement of the cutting tool 202 when the first tube 308 contacts the second segment 338 (after having cut or drilled through the anatomical element 306). In other words, the shield 304 is sized so as to block and prevent further movement of the cutting tool 202 in the first direction (as indicated by the arrow 232) upon contact of the cutting tool 202 with the shield 304. Such blocking may prevent damage to surrounding soft tissue (e.g., dura matter, nerves, etc.) or other anatomical elements when cutting or drilling an anatomical element such as bone.

The dimensions of the second segment 338 may be selected, for example, based on the dimensions of the cutting tool 202, a flexibility and/or rigidity of the cutting tool 202, and/or a cutting speed of the cutting tool 202 (e.g., to ensure that the cutting tool 202 will not cut through the second segment 338 before being stopped). In some embodiments, the cutting tool 202 may be configured to only extend as far as the second segment 338, such that the cutting tool 202 is physically unable to cut through the shield 304.

In embodiments of the present disclosure in which the system 300 comprises a fixed shield, the system 300 may be oriented prior to use so that the anatomical element to be cut is positioned in between the cutting tool 202 and the shield 304. During use, the cutting tool 202 advances toward the shield 304, and anatomical elements on an opposite side of the shield 304 are protected from harm by the shield 304. Also during use, the second tube 210 may extend to a side of the anatomical element 306 opposite the shield 304. The first tube 208 may then move from the first position (in which the plurality of teeth 228 do not extend past the second tube 210) to the second position. The first tube 208 may then engage the anatomical element 306 and rotate, oscillate, or vibrate to cut, drill, or otherwise remove a portion of the anatomical element 306. Once the first tube 208 emerges at the planned exit point (or along any portion of a cutting path or planned trajectory of the cutting tool 202), the shield 304 prevents further extension of the cutting tool 202 and protects the surrounding soft tissue.

FIGS. 4A-4C illustrate positioning of the cutting tool 202 at the anatomical element 306 and cutting the anatomical element 306 with the cutting tool 202. It will be appreciated that the positioning of the cutting tool 202 shown in FIGS. 4A-4C is applicable to the systems 200 and 300 described above with respect to FIGS. 2 and 3 or to any such systems described herein or encompassed by the present disclosure.

FIG. 4A depicts the bone cutting system 300, described above with respect to FIG. 3 in a first configuration. In the first configuration, the cutting tool 202 is positioned near the base 334 and is in a non-extended state. In other words, the first tube 208 and the second tube 210 are both spaced from the anatomical element 306. Further, the first tube 208 is shown in the first position, in which the first tube 208 does not extend past the second tube 210. In other instances, the first tube 208 may be in the second position (in which the first tube 208 extends past the second tube 210) when the system 300 is in the first configuration.

FIG. 4B depicts the bone cutting system 300 in a second configuration. In the second configuration, the cutting tool 202 is positioned at the anatomical element 306 such that the second tube 210 contacts the anatomical element 306. To move from the first configuration to the second configuration, the cutting tool 202 may be telescopically extended or may telescopically extend from the first configuration to the second configuration. Such movement may include telescopically extending both the first tube 208 and the second tube 210. As illustrated, the second tube 210 is shown in the first position. In other instances, the second tube 210 may be in the second position when the system 300 is in the second configuration and/or any period of time when the cutting tool 202 moves from the first configuration to the second configuration.

FIG. 4C depicts the bone cutting system 300 in a third configuration. In the third configuration, the second tube 210 is contacting the anatomical element 306 and the first tube 210 is cutting the anatomical element 306. In other words, the first tube 210 is in the second position in which the first tube 208 extends past the second tube 210, thereby exposing the plurality of teeth 228 for cutting.

It will be appreciated that the above-described movement of the cutting tool 202 of system 300 from a first configuration to a third configuration may describe movement of any cutting tool 202, 602 (described below) of any bone cutting system such as the bone cutting system 200, 500 or 600 (described below). Further, it will be appreciated that the bone cutting system 200, 300, 500, or 600 can have more than or fewer than three configurations.

Figure 5:
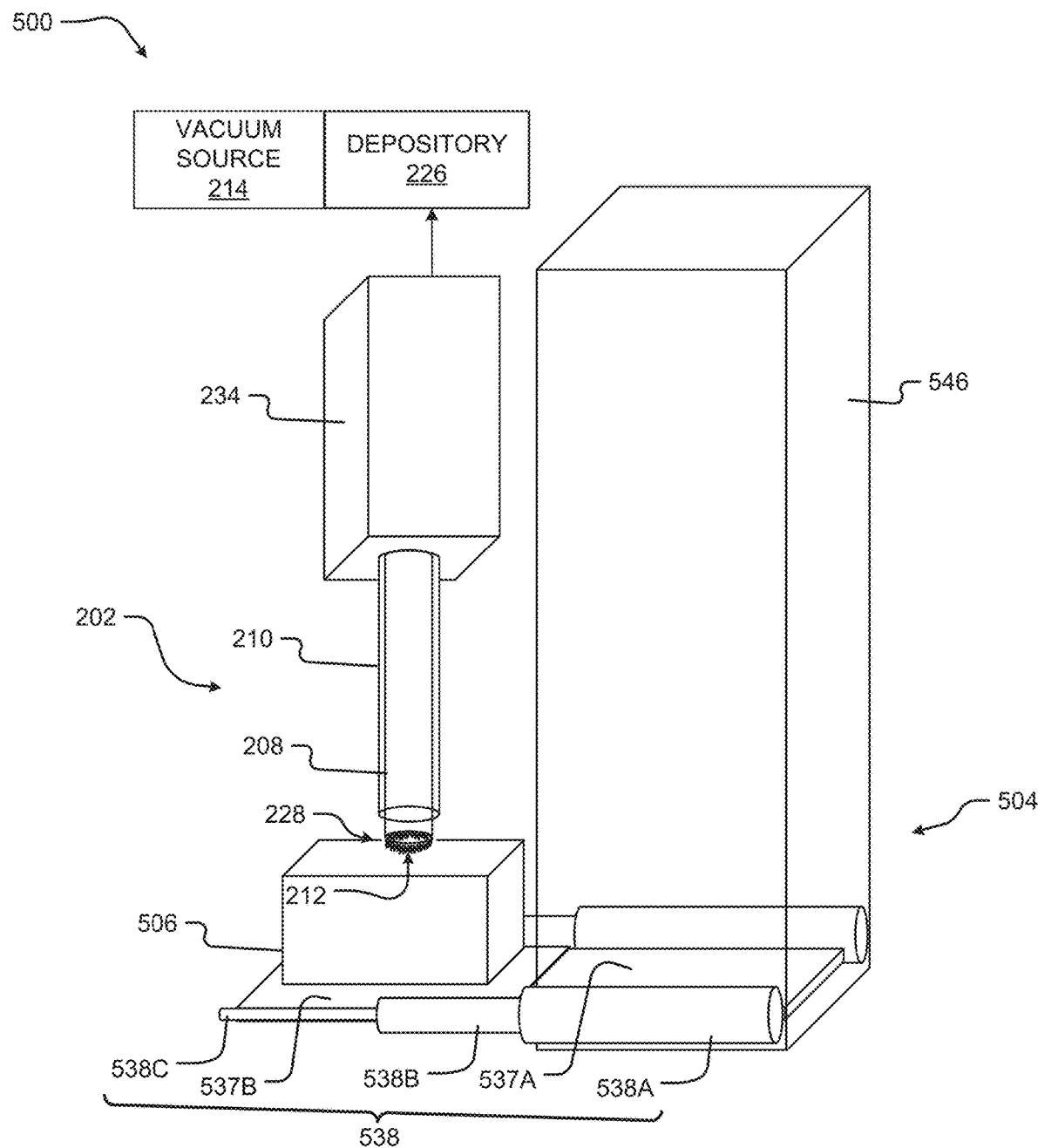
FIG. 5 is a schematic perspective view of a partial anatomical element cutting system according to at least one embodiment.
Figure 6:
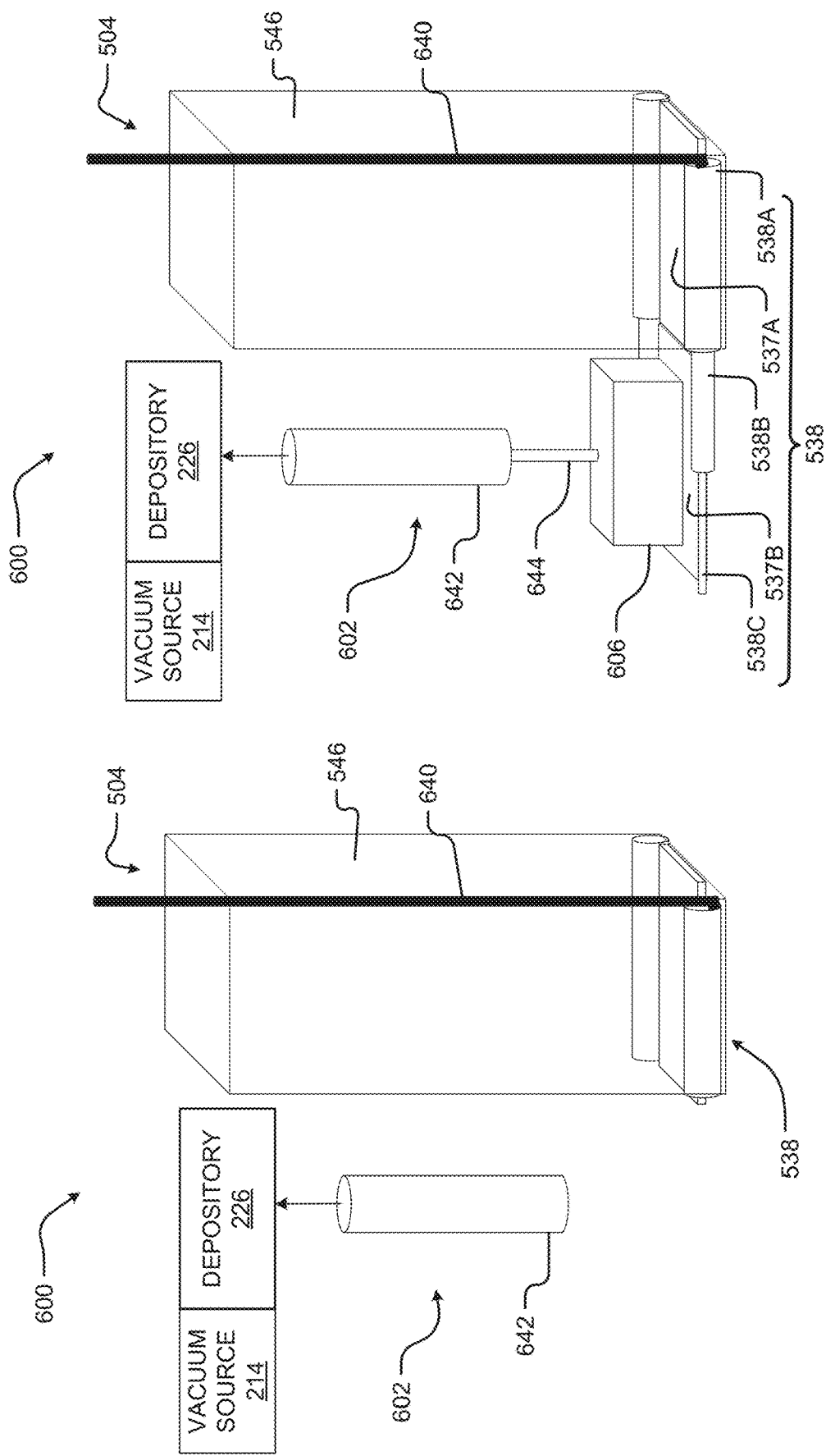
FIG. 6A is a schematic perspective view of a partial anatomical element cutting system according to at least one embodiment in a first orientation.
FIG. 6B is a schematic perspective view of the partial anatomical element cutting system of FIG. 6A in a second orientation.

Turning to FIG. 5, a schematic perspective view of a bone cutting system 500 is shown. The bone cutting system 500 may be used in a minimally invasive surgical procedure or an open surgery. Though the system 500 is referred to as a bone cutting system 500, it will be appreciated that the system 500 can be used to cut any anatomical element. Many components of the system 500 are the same as or similar to the components of the system 200, and are described above in connection with the system 200 such as, for example, the cutting tool 202, the vacuum source 214, and the depository 226.

The system 500 includes the cutting tool 202 and a shield 504. The shield 504 is separate from and therefore may be oriented independently of the cutting tool 202. In some embodiments, the cutting tool 202 may be oriented by a first robotic arm and the shield 504 may be oriented by a second robotic arm. The first robotic arm and the second robotic arm may be the same as or similar to the robotic arm 116 described above with reference to FIG. 1. In such embodiments, a first incision may be formed to receive the cutting tool 202 and a second incision may be formed to receive the shield 504 during a surgical procedure (such as, for example, a minimally invasive surgical procedure). In other embodiments, the cutting tool 202 and the shield 504 may be oriented by a user such as a surgeon or other medical provider. In further embodiments, one of the cutting tool 202 or the shield 504 may be oriented by a robotic arm such as the robotic arm 116 and the other one of the cutting tool 202 or the shield 504 may be oriented by a user.

The shield 504 may include a base 546 and a platform 538. Although shown as a rectangular prism, the base 546 (as with every other base of the present disclosure) may have any suitable shape. The platform 538 may telescopically extend or slide from a first position, in which the platform 538 does not extend past the base 546 (as shown in FIG. 6A)

to a second position, in which the platform 538 extends past the base 546 (as shown in FIG. 6B). As illustrated, the platform 538 comprises a first set of rails 538A, a second set of rails 538B, and a third set of rails 538C by which a second platform 537B slides or extends from a first platform 537A. In other embodiments, the platform 538 may include more than or fewer than three sets of rails and more than or fewer than two platforms. As shown in the illustrated embodiment, the second platform 537B is oriented at a side of the anatomical element 506 opposite the cutting tool 202 so that the third platform 538C may stop or prevent movement of the cutting tool 202 past the second platform 537B when the cutting tool 202 contacts the second platform 537B.

The second platform 537B may have a width at least as wide as a diameter of the cutting tool 202. In some embodiments, the width is about 10 mm. In other embodiments, the width is less than or greater than 10 mm. In some embodiments, the second platform 537B may also have a length at least as wide as the diameter of the cutting tool 202. In some embodiments, the length is about 25 mm. In other embodiments, the length is greater than or less than 25 mm. The second platform 537B may also have a depth of about 4 mm. In other embodiments, the depth of the second platform 537B may be less than or greater than 4 mm.

The second platform 537B is dimensioned so as to block further movement of the cutting tool 202 when the first tube 308 contacts the second platform 537B (after having cut or drilled through the anatomical element 506). In other words, the shield 504 is sized so as to block and prevent further movement of the cutting tool 202 in the first direction (as indicated by the arrow 232, shown in FIG. 2) upon contact of the cutting tool 202 with the shield 504. Such blocking may prevent damage to surrounding soft tissue (e.g., dura matter, nerves, etc.) or other anatomical elements when cutting or drilling an anatomical element such as bone.

The dimensions of the second platform 537B may be selected, for example, based on the dimensions of the cutting tool 202, a flexibility and/or rigidity of the cutting tool 202, and/or a cutting speed of the cutting tool 202 (e.g., to ensure that the cutting tool 202 will not cut through the second platform 537B before being stopped). In some embodiments, the cutting tool 202 may be configured to only extend as far as the second platform 537B, such that the cutting tool 202 is physically unable to cut through the shield 504.

Turning to FIG. 6A, a schematic perspective view of a bone cutting system 600 is shown in a first orientation. The bone cutting system 600 may be used in a minimally invasive surgical procedure or an open surgery. Though the system 600 is referred to as a bone cutting system 600, it will be appreciated that the system 600 can be used to cut any anatomical element. Many components of the system 600 are the same as or similar to the components of the systems 200 and 500, and are described above in connection with the systems 200 and 500 such as, for example, the shield 504, the vacuum source 214, and the depository 226.

The system 600 includes a cutting tool 602, the shield 504, and a line 640. The shield 504 is separate from and therefore may be oriented independently of the cutting tool 602. In some embodiments, the cutting tool 602 may be oriented by a first robotic arm and the shield 504 may be oriented by a second robotic arm. The first robotic arm and the second robotic arm may be the same as or similar to the robotic arm 116 described above with reference to FIG. 1. In such embodiments, a first incision may be formed to receive the cutting tool 602 and a second incision may be formed to receive the shield 504 during a surgical procedure (such as, for example, a minimally invasive surgical procedure). In other embodiments, the cutting tool 602 and the shield 504 may be oriented by a user such as a surgeon or other medical provider. In further embodiments, one of the cutting tool 602 or the shield 504 may be oriented by a robotic arm such as the robotic arm 116 and the other one of the cutting tool 602 or the shield 504 may be oriented by a user.

The cutting tool 602 may include a core or base 642 and a drill bit 644, shown in FIG. 6B. The drill bit 644 may be configured to telescopically extend from the core or base 642. The drill bit 644 and/or the base 642 may be made from any solid, biocompatible material such as metal, aluminum, stainless steel, steel, titanium, plastic (e.g., PEEK), or the like.

In some embodiments, the line 640 may be a pneumatic or hydraulic hose for actuating the telescopic functionality of the platform 538 (and thereby causing the platform 538 to telescopically extend or retract). In other embodiments, the line 640 may be a wire for delivering electricity to a motor that causes the platform 538 to telescopically extend or retract. In further embodiments, the line 640 may be a wire for mechanically or electrically actuating a biasing force (for example, a spring) for telescopically extending the platform 538. For example, a rigid-flex cable may be attached to an end of the platform 538 (or in some instances, a spring disposed at, for example, an end of the platform 538 or at any portion of the shield 504) whereby in pushing the wire down, the platform 538 is extended and in pulling the wire up, the platform 538 is retracted.

In FIG. 6A, the system 600 is shown in the first orientation in which the drill bit 644 is retracted in the base 642 and the platform 538 is retracted in the base 546.

In FIG. 6B, the system 600 is shown in a second orientation in which the drill bit 644 is telescopically extended from the base 642 and the platform 538 is telescopically extended from the base 546. In the second orientation, the second platform 537B is oriented at a side of the anatomical element 606 opposite the cutting tool 602 so that the second platform 537B may stop or prevent movement of the cutting tool 602 past the second platform 537B when the cutting tool 602 contacts the second platform 537B.

Though the system 600 is shown in a first orientation and a second orientation in FIGS. 6A-6B, it will be appreciated that the system 600 can include one orientation or more than two orientations.

It will be appreciated that the systems 200, 300, 500, and 600 may include any combination of any embodiment of the cutting tool and the shield. For example, the shield may have a fixed second segment as described with respect to FIG. 3 and may be oriented independently of the cutting tool as described with respect to FIG. 2. In another example, the shield may have a second segment with a selectively adjustable angle relative to the first segment as described with respect to FIG. 2 and may be oriented by a robotic arm (instead of two robotic arms) as described with respect to FIG. 3. In another example, the shield may have a telescoping second segment as described with respect to FIG. 5 and may be oriented by one robotic arm as described with respect to FIG. 3.

Figure 7:
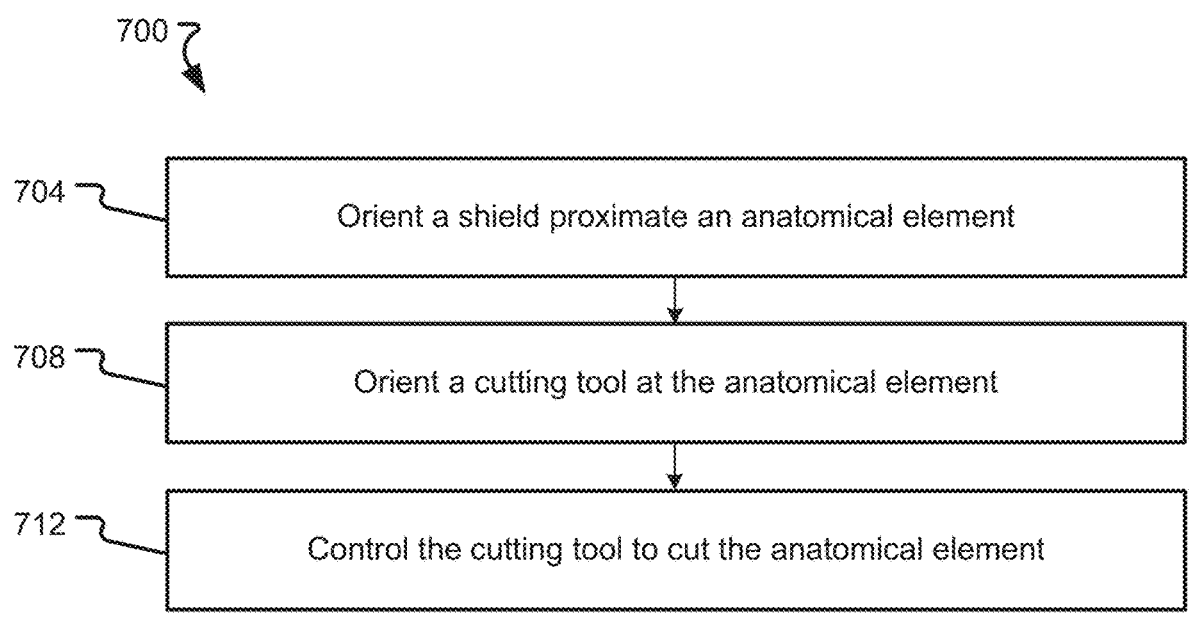
FIG. 7 is a flowchart according to at least one embodiment of the present disclosure.

FIG. 7 depicts a method 700 that may be used, for example, for cutting anatomical elements such as bone. The method 700 may be used, for example, during a minimally invasive surgical procedure. The procedure may be, for example, a decompression procedure, a laminectomy, or a laminotomy. The method 700 may also be used during an open surgical procedure.

The method 700 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 700. The at least one processor may perform the method 700 by executing instructions such as the instructions 122 stored in a memory such as the memory 106. The instructions may correspond to one or more steps of the method 700 described below.

The method 700 comprises orienting a shield proximate an anatomical element (step 704). The shield may be the same as or similar to the shield 204, 304, or 504 described above with respect to FIG. 2, 3, or 5, respectively. The anatomical element may be, for example, any hard tissue such as bone. The anatomical element may be, in some embodiments, a vertebra. In some embodiments, the shield may be oriented by a robotic arm such as the robotic arm 116 as described with respect to FIG. 1 above. In other embodiments, the shield may be oriented by a user such as a surgeon or other medical provider. The shield may be oriented proximate the anatomical element at a planned exit point of a cutting tool. In other instances, the shield may be positioned along any portion of a cutting path of the cutting tool. The cutting tool may be the same as or similar to the cutting tool 202 or 602 described above with respect to FIG. 2 or 6, respectively. The cutting tool may include a first tube nested inside of a second tube. The first tube may include a distal end comprising a set or plurality of cutting teeth for cutting the anatomical element. At least one of the first tube and/or the second tube may be configured to extend in a first direction. The cutting tool may also be or comprise a drill bit such as the drill bit 644.

In embodiments where the shield includes a base, orienting the shield may include positioning a base of the shield. Positioning the base of the shield may include simply positioning the base of the shield at an incision. In other instances, positioning the base of the shield may include maneuvering the base of the shield along a trajectory into the incision. In instances where a first segment of the shield may telescope, positioning the base of the shield may also include maneuvering the base of the shield in order to insert at least a portion of the first segment into an incision when the portion needs to be inserted into the incision prior to telescoping. In these instances, it will be appreciated that the shield may be any shield described herein, such as, for example, the shield 204, 304, 504, and that such shield may telescope in any embodiment. In some embodiments, the shield may be separate from the cutting tool, as shown and described in FIGS. 2, 5, and 6A-6B. In other embodiments, the shield and the cutting tool may be combined, as described with respect to FIG. 3. Orienting the shield may also include causing a portion of the shield to extend linearly, whether telescopically (e.g., a first segment, a second segment, and/or a platform) or otherwise. For example, when the shield is similar to or the same as the shield 504, the platform may extend telescopically into position. Orienting the shield may also include causing one portion of the shield (e.g., a second segment) to rotate relative to another portion of the shield (e.g., a first segment). For example, when the shield is similar to or the same as the shield 204, the second segment may rotate into position.

The shield may be oriented at a shield pose (e.g., position and orientation). In some embodiments, the shield pose may be based on a surgical plan such as the surgical plan 120. In other embodiments, the shield pose may be input received from a user such as a surgeon or other medical provider. The surgical plan and/or the input may be received from a user interface such as the user interface 110 and stored in a memory such as the memory 106. Instructions such as the instructions 122 may be generated based on the surgical plan and/or the input. In some embodiments, the instructions may be machine readable and transmitted to the robotic arm to cause the robotic arm to orient the shield at the shield pose. In other embodiments, the instructions may be human readable and displayed on the user interface, for example, and include instructions for a user to orient the shield at the shield pose.

The method 700 also comprises orienting the cutting tool at the anatomical element (step 708). The cutting tool may be positioned at a side of the anatomical element opposite the shield as oriented in step 704. In some embodiments, a user such as a surgeon or other medical provider may orient the cutting tool at the anatomical element. In other embodiments, a robotic arm such as the robotic arm 116 may orient the cutting tool at the anatomical element. In some embodiments, the robotic arm is the same robotic arm as the robotic arm orienting the shield in step 704. In other embodiments, the robotic arm is a different robotic arm than the robotic arm orienting the shield. In such embodiments, the shield may be oriented independently of the cutting tool.

The cutting tool may be oriented at a cutting tool pose (e.g., position and orientation). In some embodiments, the cutting tool pose may be based on a surgical plan such as the surgical plan 120, and may be based on a trajectory defined in the surgical plan. In other embodiments, the cutting tool pose may be defined by input received from a user such as a surgeon or other medical provider. The surgical plan and/or the input may be received from a user interface such as the user interface 110 and stored in a memory such as the memory 106. Instructions such as the instructions 122 may be generated based on the surgical plan and/or the input. In some embodiments, the instructions may be machine readable and transmitted to the robotic arm to cause the robotic arm to orient the cutting tool at the cutting tool pose. In other embodiments, the instructions may be human readable and displayed on the user interface, for example, and include instructions for a user to orient the cutting tool at the cutting tool pose.

The step 708 may also include extending (whether by a robotic arm or a user) the second tube of the cutting tool in a first direction to orient the cutting tool at the cutting tool pose. During such instances, the first tube may not extend past the second tube. In other words, the plurality of teeth may not be exposed and may not extend past the second tube. The step 708 may also include moving the first tube from a first position, in which the first tube does not extend past the second tube, to a second position, in which the first tube (and thus, the plurality of teeth) extend past the second tube.

In some embodiments of the present disclosure, the cutting tool may comprise a sheath or other covering (such as, for example, the second tube 210, a retractable cap, or a cover through which the plurality of teeth 228 cut) over one or more cutting portions thereof (such as, for example, the plurality of teeth 228 disposed on the first tube 208). In such embodiments, the sheath may be positioned over the one or more cutting portions during the step 708. In other embodiments, however, the cutting tool may not comprise a sheath or other covering for the one or more cutting portions thereof, and which one or more cutting portions may be exposed during orientation of the cutting tool.

For the avoidance of doubt, the steps 704 and 708 may occur in sequence or simultaneously. In some embodiments, the cutting tool may be oriented prior to orientation of the shield, while in other embodiments, the shield may be oriented prior to orientation of the cutting tool. Where the cutting tool is first oriented, the orientation of the shield may be based on the orientation of the cutting tool. Where the shield is first oriented, the orientation of the shield may be based on a planned orientation of the cutting tool.

The method 700 also comprises controlling the cutting tool to cut the anatomical element (step 712). As previously described, in embodiments where the cutting tool comprises a first tube and a second tube (as in the systems 200, 300, and 500 described above), when the first tube is in the second position, the plurality of teeth are exposed and prepared for engagement with the anatomical element. The first tube may use rotational movement, vibrational movement, or oscillations to scrape, crush, drill, or otherwise cut the anatomical element. In some embodiments, a robotic arm such as the robotic arm 116 may control the cutting tool to cut through the anatomical element toward the planned exit point or along a cutting trajectory. In other embodiments, a user such as a surgeon or other medical provider may cause the cutting tool to cut the anatomical element toward the planned exit point or along a cutting trajectory. The cutting trajectory may include extending the first tube in the first direction. Once the cutting tool has breached the anatomical element, the shield prevents further movement of the cutting tool in the first direction, along the trajectory, and/or beyond the point of exit of the cutting tool from the anatomical element, by presenting a physical barrier to further forward movement and/or cutting of the cutting tool. In some embodiments, the cutting tool may cease cutting (whether by ceasing a rotational movement, a vibrational movement, or oscillation) when the cutting tool contacts the shield. In such embodiments, the robotic arm may automatically cause the cutting tool to cease cutting. In other embodiments, the user may cause the cutting tool to cease cutting (whether by releasing a trigger, pressing a stop button, or instructing the robotic arm to cause the cutting tool cease cutting).

The cutting tool may cut the anatomical element for a predetermine period of time, to a predetermined depth, and/or based on any other predetermined cutting parameter. In some embodiments, one or more predetermined cutting parameters, the planned exit point, and/or the cutting trajectory may be based on a surgical plan such as the surgical plan 120. In other embodiments, the one or more predetermined cutting parameters, the planned exit point, and/or the cutting trajectory may be defined by input received from a user such as a surgeon or other medical provider. The surgical plan and/or the input may be received from a user interface such as the user interface 110 and stored in a memory such as the memory 106. Instructions such as the instructions 122 may be generated based on the surgical plan and/or the input. In some embodiments, the instructions may be machine readable and transmitted to the robotic arm to cause the robotic arm to cause the cutting tool to cut the anatomical element along a trajectory toward the planned exit point or along the cutting trajectory based on one or more predetermined cutting parameters. In other embodiments, the instructions may be human readable and displayed on the user interface, for example, and include instructions for a user to cause the cutting tool to cut the anatomical element toward the planned exit point or along the cutting trajectory based on one or more predetermined cutting parameters.

The present disclosure encompasses embodiments of the method 700 that comprise more or fewer steps than those described above, and/or one or more steps that are different than the steps described above.

As noted above, the present disclosure encompasses methods with fewer than all of the steps identified in FIG. 7 (and the corresponding description of the method 700), as well as methods that include additional steps beyond those identified in FIG. 7 (and the corresponding description of the method 700). The present disclosure also encompasses methods that comprise one or more steps from one method described herein, and one or more steps from another method described herein.

Although the present disclosure describes cutting tools having mechanical cutting implements (e.g., saws or other sharp and/or serrated edges, drill bits), aspects of the present disclosure are applicable to energy-based cutting tools as well. For example, a shield as disclosed herein may be used in connection with an ablation probe, a laser cutting device, or any other energy-based cutting tool to protect anatomical elements or tissue at risk of collateral damage during use of the tool.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for cutting bone comprising:
   a cutting tool configured to rotate;
   a shield;
   a first robotic arm configured to hold the cutting tool;
   a second robotic arm configured to hold the shield;
   a processor; and
   a memory storing instructions for execution by the processor that, when executed, cause the processor to:
   cause the second robotic arm to orient the shield proximate an anatomical element along a cutting path of the cutting tool.

2. The system of claim 1, wherein the cutting tool is configured to extend in a first direction, wherein the shield comprises a first body configured to extend in a second direction and a second body coupled to the first body by a joint, the second direction distinct from the first direction, the second body configured to selectively rotate about the joint.

3. The system of claim 1, wherein the cutting tool comprises a first tube nested inside of a second tube, the first tube having a distal end comprising a set of cutting teeth.

4. The system of claim 3, further comprising:
   a vacuum source configured to apply a suction force to the cutting tool to suction anatomical particles through the first tube.

5. The system of claim 3, wherein the first tube is configured to extend axially.

6. The system of claim 1, wherein the shield has a width at least as wide as a diameter of the cutting tool.

7. The system of claim 1, wherein a diameter of the cutting tool is about 10 mm.

8. A system for cutting bone comprising:
   a cutting tool supported by a robotic arm;
   a shield supported by the robotic arm;
   a processor; and
   a memory storing instructions for execution by the processor that, when executed, cause the processor to:
   cause the robotic arm to orient the shield proximate an anatomical element at a planned exit point of the cutting tool, and to control the cutting tool to cut through the anatomical element toward the planned exit point.

9. The system of claim 8, wherein at least one of a cutting tool and the shield is configured to extend telescopically.

10. The system of claim 8, wherein the cutting tool comprises a first tube nested inside of a second tube, the first tube configured to extend from the second tube, the first tube having a distal end comprising a set of cutting teeth.

11. The system of claim 10, wherein causing the robotic arm to orient the cutting tool includes extending the second tube to orient the cutting tool at the side of the anatomical element, wherein the first tube does not extend past the second tube.

12. The system of claim 8, wherein the shield comprises a first segment and a second segment disposed at an angle to the first segment.

13. The system of claim 12, wherein the second segment is perpendicular to the first segment.

14. The system of claim 12, wherein the first segment and the second segment are fixed.

\* \* \* \* \*